(12) United States Patent
Douglas

(10) Patent No.: US 10,959,696 B1
(45) Date of Patent: Mar. 30, 2021

(54) METHOD AND APPARATUS FOR AN IMPROVED LOCALIZER FOR 3D IMAGING

(71) Applicant: Robert Edwin Douglas, Winter Park, FL (US)

(72) Inventor: Robert Edwin Douglas, Winter Park, FL (US)

( * ) Notice: Subject to any disclaimer, the term of this patent is extended or adjusted under 35 U.S.C. 154(b) by 0 days.

(21) Appl. No.: 17/100,902

(22) Filed: Nov. 22, 2020

Related U.S. Application Data

(63) Continuation-in-part of application No. 16/785,606, filed on Feb. 9, 2020.

(60) Provisional application No. 62/939,685, filed on Nov. 25, 2019, provisional application No. 62/940,822, filed on Nov. 26, 2019.

(51) Int. Cl.
| | | |
|---|---|---|
| *A61B 6/00* | (2006.01) | |
| *A61B 6/03* | (2006.01) | |
| *G06T 7/62* | (2017.01) | |
| *A61N 5/10* | (2006.01) | |

(52) U.S. Cl.
CPC ............ *A61B 6/5223* (2013.01); *A61B 6/032* (2013.01); *A61B 6/466* (2013.01); *A61B 6/468* (2013.01); *A61N 5/103* (2013.01); *G06T 7/62* (2017.01); *G06T 2207/10081* (2013.01); *G06T 2207/20036* (2013.01); *G06T 2207/20081* (2013.01); *G06T 2207/20084* (2013.01); *G06T 2207/30096* (2013.01)

(58) Field of Classification Search
None
See application file for complete search history.

(56) References Cited

U.S. PATENT DOCUMENTS

| | | | | |
|---|---|---|---|---|
| 8,303,505 | B2 * | 11/2012 | Webler | G16H 50/50 |
| | | | | 600/447 |
| 10,133,348 | B2 * | 11/2018 | Lu | G06K 9/00604 |
| 2011/0141103 | A1 * | 6/2011 | Cohen | G02B 21/367 |
| | | | | 345/419 |
| 2016/0345925 | A1 * | 12/2016 | Westerhoff | A61B 6/032 |
| 2017/0337693 | A1 * | 11/2017 | Baruch | G06T 7/194 |
| 2018/0268552 | A1 * | 9/2018 | Wood | G06K 9/4628 |
| 2019/0172197 | A1 * | 6/2019 | Buckler | A61B 6/032 |
| 2019/0236851 | A1 * | 8/2019 | Tomori | G06F 3/04842 |
| 2019/0340751 | A1 * | 11/2019 | Kim | A61B 6/463 |
| 2020/0069971 | A1 * | 3/2020 | Sasaki | A61B 8/5269 |
| 2020/0265618 | A1 * | 8/2020 | Chen | G06T 11/008 |

\* cited by examiner

*Primary Examiner* — James A Thompson

(57) ABSTRACT

This patent includes a method for performing precision localization within the body on a cross-sectional imaging examination. As a result of the improved precision localization techniques, anatomic structure specific coordinate systems can be developed to improve radiological analysis.

19 Claims, 19 Drawing Sheets

A SMART LOCALIZATION SYSTEM

Prior Art

Prior Art

DETERMINING THE CORRESPONDING FIRST COORDINATE

Techniques to determine the corresponding first coordinate

- Performing segmentation to determine a structure at the site of a cursor. If the localizer is inside the boundary of the left adrenal gland, then the smart localizer system would show a point inside the left adrenal gland in another image.

- Use of landmarks, registration points, pseudoregistration points. Examples of landmarks would include a single coarse calcification within the spleen, which could readily be recognized. An example of registration point would include the center point of an organ. An example of a pseudoregistration point would be a point that has a defined distance between two registration points.

- Use of an organ-specific coordinate system. An organ based coordinate system can be established to improve localization by defining precise coordinates within an organ. For example, a spherical coordinate system can be performed for the liver wherein the origin is defined as the center point.

- Perform an artificial intelligence algorithm, which utilizes training data comprises sets of longitudinal 3D imaging examinations with embedded localization points (e.g., an example would be a CT dataset from 2019 with a point on a left adrenal gland and a CT dataset from 2018 with a corresponding point on the left adrenal gland). A key point of novelty is the use of point and corresponding point as part of the training dataset.

Figure 5

A SMART LOCALIZATION SYSTEM

DISPLAYING THE CORRESPONDING FIRST COORDINATE

Display options for the digital object for the corresponding first coordinate

Appearance
- Variable color / grayscale (e.g., red, blue, white, yellow)
- Variable size (e.g., 0.5 mm, 1 cm)
- Variable shape (e.g., round, star)
- Other variations (e.g., blinking, solid, etc.)

Timing
- Show at all times
- Show only when user is looking at the monitor displaying the first coordinate (which is advantageous because the user would not see a mobile object in the periphery of the visual field)

Figure 7

IMPROVEMENTS VIA AN ORGAN-SPECIFIC COORDINATE SYSTEM

Analysis techniques enabled

Accruate voxel-by-voxel analysis
•Perform comparative analysis of interval change between voxel and/or cluster of voxels at the first imaging examination with voxel and/or cluster of voxels at the second examination (e.g., generating organ-specific coordinate system so that each voxel in the segmented organ has a specific coordinate that is reproducible within the organ)

Enhanced accuracy during radiation treatment
•An organ-specific coordinate system will enable precision localization of a small lesion (e.g., 1 cm) within the liver.

Enhanced accuracy during surgery
•An organ-specific coordinate system will enable precision localization of a small lesion (e.g., 1 cm) within the liver.

Figure 8

ILLUSTRATION OF PRECISION LOCALIZATION

ILLUSTRATION OF ORGAN-SPECIFIC COORDINATE SYSTEM

ILLUSTRATION OF ORGAN-SPECIFIC COORDINATE SYSTEMS
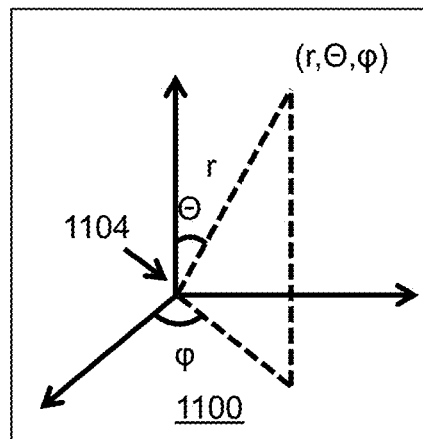
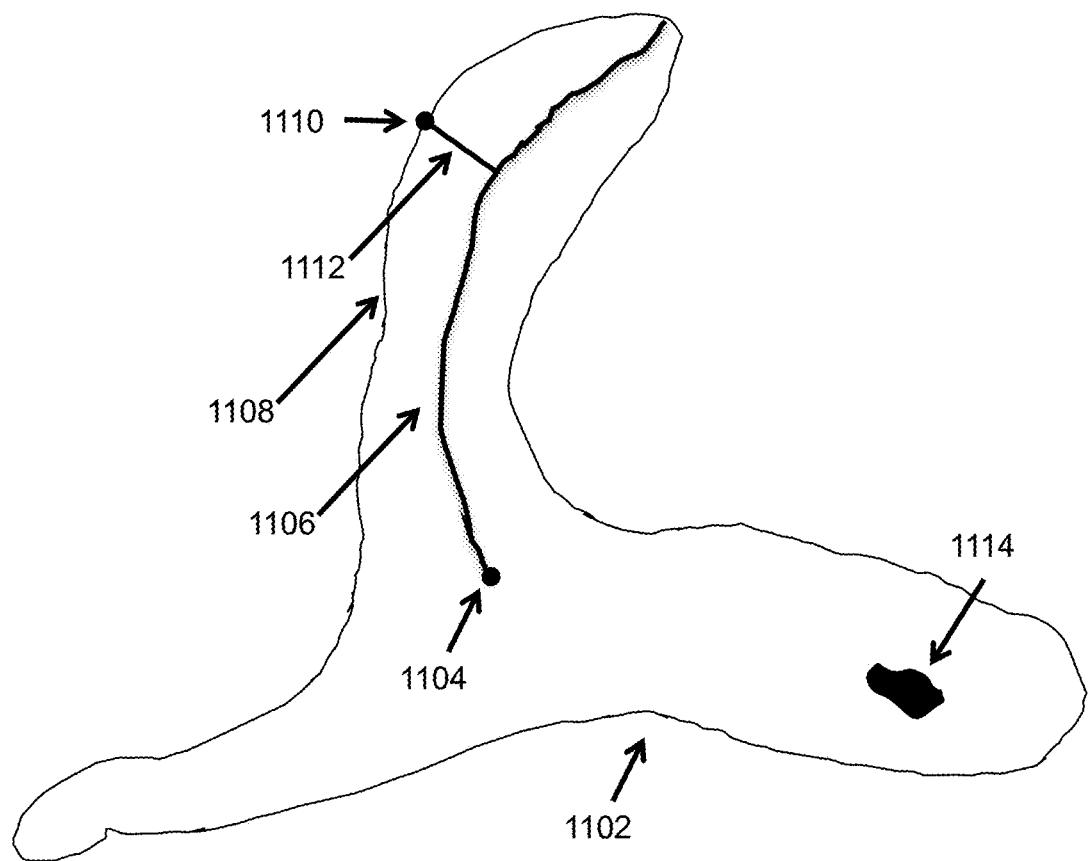
Figure 11

PSEUDO REFERENCE POINTS AND ENSUING ANALYSIS

VOXEL-BY-VOXEL ANALYSIS

| Organ specific voxel coordinate | Time Point #1 | Time Point #2 | Time point #3 |
|---|---|---|---|
| (0,0,0) | 40 | 41 | 40 |
| (0.1mm, 0,0) | 40 | 40 | 90 |
| (0.2mm, 0,0) | 40 | 41 | 40 |
| ... | | | |

Figure 13

TRACKING A SPECIFIC LESION IN AN ORGAN THAT IS CHANGING IN SIZE

TRACKING A SPECIFIC LESION IN AN ORGAN THAT IS
CHANGING IN ORIENTATION

TRACKING A SPECIFIC LESION IN AN ORGAN THAT IS
CHANGING IN CONFIGURATION

ORGAN-SPECIFIC COORDINATE SYSTEM ENABLES INTER-ORGAN ANGULAR MEASUREMENTS

VARIOUS COORDINATE SYSTEMS CAN BE USED WITHIN AN ORGAN

METHOD AND APPARATUS FOR AN IMPROVED LOCALIZER FOR 3D IMAGING

CROSS-REFERENCES TO RELATED APPLICATIONS

This patent application is a continuation-in-part of U.S. patent application Ser. No. 16/785,606 filed on Feb. 9, 2020 and claims the benefit of U.S. Provisional Application 62/939,685 filed on Nov. 25, 2019 and U.S. Provisional Application 62/940,822 filed on Nov. 26, 2019.

TECHNICAL FIELD

This patent application applies to the field of 3D imaging.

BACKGROUND

The field of 3D visualization is growing rapidly in medicine, military, video games and many other industries.

SUMMARY

All examples, aspects and features mentioned in this document can be combined in any technically possible way.

Methods disclosed in the patent are provided to overcome some of the difficulties that are faced during localization of 3D imaging of complex datasets.

A first difficulty is discussed in medical imaging. A radiologist may describe using language where a lesion is located. For example, a sentence may state "an indeterminate T2 hyperintensity in the right frontal lobe." But, if the radiologist just said that, another physician may be left with the question of "where in the right frontal lobe." Assume the radiologist tried harder and said "an indeterminate T2 hyperintensity in the superior frontal gyms of the right frontal lobe." Still, a reader of the radiology report could ask "where precisely in the superior frontal gyms of the right frontal lobe?" For this reason, radiologist sometimes leave an image number along side of the description of their finding, yet a number can be inadequate. For example, the radiologist states "in the superior frontal gyms of the right frontal lobe (series 4: image 120)". Another radiologist and referring clinician might still be left wondering what exactly was that radiologist referring to?

A second difficulty is discussed in medical imaging. Current localization strategies utilize a matrix (e.g., 512× 512) and a series of CT slices. When a user performs localization from a CT scan at a first time point to a CT scan at a second time point, the localizer performs localization based on slice number and pixel coordinate. Since a patient's anatomy comprises soft tissues that are deformable and since the patient may be angled or positioned slightly different on two different examinations, the anatomy does not perfectly align. For example, if a user using a current PACS localization process performs slice sync, scrolls to a spot and subsequently performs localization of the right adrenal gland from a 2019 examination to a 2020 examination, the localization digital object localizes to a slice and a pixel coordinate, but the slice may not even include the adrenal gland and furthermore even if the slice did include the adrenal gland, the localizer would not necessarily be positioned on the right adrenal gland in the 2020 examination. The methods and apparatuses disclosed in this patent provide an improved localization. The methods disclosed provide a GPS like system for the human body.

The preferred embodiment loads a first 3D imaging dataset into an image processing workstation wherein the first 3D dataset comprises a voxelated dataset of a scanned volume at a first time point. Additionally, the preferred embodiment loads a second 3D imaging dataset into the image processing workstation wherein the second 3D dataset comprises a voxelated dataset of the scanned volume at a second time point. Additionally, the preferred embodiment performs segmentation of the first 3D imaging dataset to define a structure. Additionally, the preferred embodiment performs segmentation of the second 3D imaging dataset to define the structure. Additionally, the preferred embodiment performs a smart localization system comprising: positioning a cursor on a first coordinate of an image of the first 3D dataset, wherein the first coordinate is enclosed within the structure, and wherein the first coordinate is located at a sub-structure location. A sub-structure location is a location inside the structure. Additionally, the preferred embodiment determines a corresponding first coordinate in the second 3D dataset, wherein the corresponding first coordinate is enclosed within the structure, wherein the corresponding first coordinate is located at the sub-structure location. Additionally, the preferred embodiment displays a digital object at the corresponding first coordinate in an image of the second 3D dataset. An alternative embodiment is to display an imaging slice of the second 3D dataset containing the sub-structure.

In order to accomplish this, the organ must be segmented such that the boundaries of the organ are properly defined. For example, in the abdomen, each solid organ (e.g., liver, spleen, gallbladder, pancreas, etc.) would be segmented such that its margins are well-defined and the inner aspects of the organ are contained in a volume. For example, the liver capsule would be the outer margin of the liver and the liver parenchyma would be in the inside of the volume.

Additionally, the coordinates of the outer margin of the organ may aid in this method's precision localization. For example, the coordinates at the top slice of the organ that demarcate the outer margins of the organ based on the segmentation method applied above should be recorded. For example, for a particular axial slice (z-value is fixed), the each (x,y) coordinate at the perimeter of the organ should be recorded and matched with the z-coordinate of the axial slice. This process is repeated for each axial slice until at which point all (x,y,z) coordinates at the boundary of the organ are recorded. Note that this reference point has a traditional (x,y,z) coordinate in each examination, but will serve to be the critical, reproducible reference points for the boundaries of the organ for the organ-specific coordinate system which will serve to register the organ over multiple examinations.

Note that the described reference points have traditional (x,y,z) coordinates in each examination, but will serve to be the critical, reproducible reference points for the organ-specific coordinate system which will serve to register the organ center over multiple examinations.

Some embodiments comprise utilizing in the smart localization system at least one reference point within the structure comprising wherein the at least one reference point is selected from the group consisting of: a center point; a superior most point; an inferior most point; a medial most point; a lateral most point; an anterior most point; a posterior most point; and a recognizable anatomic feature.

Alternative embodiments would be to select the superior most voxel, anterior most voxel or other algorithms could be used to achieve reproducible reference points. In organs wherein the internal parenchyma demonstrates recognizable features, the internal sub-structures can serve as precision landmarks and registration point(s). For example, in the liver the internal sub-structure of the middle hepatic vein can be used. For example, in the brain, the center point of the caudate head can be used.

Some embodiments comprise wherein the at least one reference point is used for at least one of the group consisting of: volumetric analysis; and, morphologic analysis.

Some embodiments comprise utilizing at least one pseudoreference point within the structure comprising wherein the at least one pseudoreference point is a distance in between at least two reference points.

Some embodiments comprise wherein the at least one pseudoreference point is used for at least one of the group consisting of: volumetric analysis; and, morphologic analysis.

Some embodiments comprise utilizing in the smart localization system a coordinate system for the structure based comprising at least one of the group consisting of: a cartesian coordinate system; a cylindrical coordinate system; a polar coordinate system; a spherical coordinate system; and an organ specific coordinate system.

Some embodiments comprise assigning a precision location of a lesion wherein the precision location comprises a coordinate location on the coordinate system.

Some embodiments comprise inputting the precision location of the lesion in a radiology report.

Some embodiments comprise inputting an annotation at the site of the precision location of the lesion on an image.

Some embodiments comprise generating at least two coordinate systems for the structure.

Some embodiments comprise using the coordinate system for at least one of the group consisting of: a radiation treatment; and a surgical procedure.

Some embodiments comprise wherein when the structure changes in size from the first 3D dataset to the second 3D dataset, the determining of the corresponding first coordinate in the second 3D dataset accounts for the structure's changes in size.

Some embodiments comprise wherein when the structure changes in configuration from the first 3D dataset to the second 3D dataset, the determining of the corresponding first coordinate in the second 3D dataset accounts for the structure's changes in configuration.

Some embodiments comprise wherein when the structure changes in orientation from the first 3D dataset to the second 3D dataset, the determining of the corresponding first coordinate in the second 3D dataset accounts for the structure's changes in orientation.

Some embodiments comprise determining a reference axis for the volume in the first 3D dataset; determining an axis of the structure in the first 3D dataset; determining a first angle wherein the first angle is an angle between the reference axis for the volume in the first 3D dataset and the axis of the structure in the first 3D dataset; determining a corresponding reference axis for the volume in the second 3D dataset; determining a corresponding axis of the structure in the second 3D dataset; determining a second angle wherein the second angle is an angle between the corresponding reference axis for the volume in the second 3D dataset and the corresponding axis of the structure in the second 3D dataset; and comparing the first angle with the second angle to determine an interval change.

Some embodiments comprise performing an analysis of interval change between a voxel at the sub-structure in the first 3D dataset and a voxel at the sub-structure in the second 3D dataset.

Some embodiments comprise determining the corresponding first coordinate by utilizing an artificial intelligence system, wherein the artificial intelligence system utilizes training data comprises sets of longitudinal 3D imaging examinations with embedded localization points.

Some embodiments comprise a non-transitory computer readable medium having computer readable code thereon for image processing, the medium comprising: performing segmentation of a first 3D imaging dataset to define a structure wherein the first 3D dataset comprises a voxelated dataset of a scanned volume at a first time point; performing segmentation of a second 3D imaging dataset to define the structure wherein the second 3D dataset comprises a voxelated dataset of the scanned volume at a second time point; performing a smart localization system comprising: positioning a cursor on a first coordinate of an image of the first 3D dataset, wherein the first coordinate is enclosed within the structure, and wherein the first coordinate is located at a sub-structure location; and determining a corresponding first coordinate in the second 3D dataset, wherein the corresponding first coordinate is enclosed within the structure, wherein the corresponding first coordinate is located at the sub-structure location; and displaying a digital object at the corresponding first coordinate in an image of the second 3D dataset.

This method teaches a process to develop an organ specific coordinate system and a method to precision localization of which anatomic feature on a first examination corresponds to which anatomic feature on a subsequent examination. Specifically, by implementing the methods disclosed in this patent, the user will be able to click a mouse on a particular punctate structure on a prior examination and then a localizer pop-up will appear on the adjacent monitor showing the precise location of the localizer on the subsequent examination. For example, the user would be able to click on the right lateral most tip of the L4 transverse process and processes disclosed in this patent will enable a pop-up to appear on the subsequent examination precisely at the right lateral most tip of the L4 transverse process. This example was to convey in the most straight forward process the overall goal of the system. In practice, however, the radiologist might click on a new tiny hypodense lesion in the liver on a CT scan and wonders whether it was present on the prior examinations? The radiologist will be able to click on the hypodense lesion and by applying methods disclosed in this patent, the system will show a pop-up icon on the prior examination at the exact corresponding spot and the radiologist will be able to tell in an instant whether the hypodense lesion is new or not. The saves time by reducing scrolling. Current systems are only able to link slices; thus, this algorithm will improve the radiologist's ability to track lesions over time. In the preferred embodiment, this process of organ specific coordinate system would be performed for all organs in the body.

It should be noted that some organs are relatively fixed in location (e.g., kidney since it is relatively fixed in the retroperitoneum). Note that other organs are relatively mobile in location (e.g., liver which is somewhat more mobile relating to diaphragmatic motion). Techniques of the smart localization system disclosed herein provide accurate localization of both fixed and mobile organs.

In some embodiments, at least one, but preferably multiple reference point within the organ may be established. Reference point(s) can be identifiable and reproducible, so that the organ specific coordinate system can be established repeatedly over multiple examinations, even when the solid organ is in different configurations or positions. The reference point may be determined by human (e.g., radiologist) or by a computer through a software (e.g., Artificial Intelligence) program.

In some embodiments, the center point of an organ is used as a reference point. The preferred embodiment would be to, after the segmentation has been performed, assign the center point of the organ by the following process. Consider a voxelated 3D dataset of a CT Scan wherein each voxel has a data unit and an x, y, z coordinate. Record the maximum x-value and minimum x-value of the organ. Then make the x-coordinate of the center, called centerX, of the organ at the half-way point between the maximum x-value and minimum x-value of the organ. Next, record the maximum y-value and minimum y-value of the organ. Then make the y-coordinate of the center, called centerY, of the organ at the half-way point between the maximum y-value and minimum y-value of the organ. Record the maximum z-value and minimum z-value of the organ. Then make the z-coordinate of the center, called centerZ, of the organ at the half-way point between the maximum Z-value and minimum Z-value of the organ. Thus, using this preferred embodiment, the center of the organ would be located at (centerX, centerY, centerZ).

In some embodiments, points other than the center should be used as a reference point. For example, consider the breast. Specifically, the preferred embodiment for the reference point for the breast is the nipple, since physicians are already accustomed to using this as a reference point. Another embodiment is to select reference points could be an imaging feature inside the organ, which is easily recognizable (e.g., surgical clip). Another embodiment is to select reference points corresponding to a reproducibly placed skin marker (e.g., BB marker over a birthmark).

Another embodiment would be to select reference points with an organ in close proximity to a fixed (i.e., non-mobile) structure. For example, the bladder is securely fixed inferiorly to the prostate gland, so using this embodiment, a reference point near the base of the bladder could be performed.

Some embodiments use an adaptable smart localization system as described above with traditional methods. For example, if a 2019 examination includes the right kidney and a 2020 examination does not (e.g., the patient has had a right nephrectomy), the smart localization system can signal to the user (e.g., via pop up) that the right kidney is no longer present. A localizer could be programmed to be placed in the right renal fossa, which would give the user context.

It should be noted that these techniques can be applied to non-medical applications, such examining 3D datasets for change, such as monitoring glaciers or ice burgs for purposes of climate change. A wide range of non-medical applications are also possible, such as those discussed in U.S. Provisional 62/940,822, which is incorporated by reference in its entirety.

Still other embodiments include a computerized device, configured to process all the method operations disclosed herein as embodiments of the invention. In such embodiments, the computerized device includes a memory system, a processor, communications interface in an interconnection mechanism connecting these components. The memory system is encoded with a process that provides steps explained herein that when performed (e.g., when executing) on the processor, operates as explained herein within the computerized device to perform all of the method embodiments and operations explained herein as embodiments of the invention. Thus, any computerized device that performs or is programmed to perform processing explained herein is an embodiment of the invention.

Other arrangements of embodiments of the invention that are disclosed herein include software programs to perform the method embodiment steps and operations summarized above and disclosed in detail below. More particularly, a computer program product is one embodiment that has a computer-readable medium including computer program logic encoded thereon that when performed in a computerized device provides associated operations providing steps as explained herein.

The computer program logic, when executed on at least one processor with a computing system, causes the processor to perform the operations (e.g., the methods) indicated herein as embodiments of the invention. Such arrangements of the invention are typically provided as software, code and/or other data structures arranged or encoded on a computer readable medium such as an optical medium (e.g., CD-ROM), floppy or hard disk or other a medium such as firmware or microcode in one or more ROM or RAM or PROM chips or as an Application Specific Integrated Circuit (ASIC) or as downloadable software images in one or more modules, shared libraries, etc. The software or firmware or other Such configurations can be installed onto a computerized device to cause one or more processors in the computerized device to perform the techniques explained herein as embodiments of the invention. Software processes that operate in a collection of computerized devices, such as in a group of data communications devices or other entities can also provide the system of the invention. The system of the invention can be distributed between many software processes on several data communications devices, or all processes could run on a small set of dedicated computers, or on one computer alone.

It is to be understood that the embodiments of the invention can be embodied strictly as a software program, as software and hardware, or as hardware and/or circuitry alone. Such as within a data communications device. The features of the invention, as explained herein, may be employed in data processing devices and/or software systems for such devices. Note that each of the different features, techniques, configurations, etc. discussed in this disclosure can be executed independently or in combination. Accordingly, the present invention can be embodied and viewed in many different ways. Also, note that this Summary section herein does not specify every embodiment and/or incrementally novel aspect of the present disclosure or claimed invention. Instead, this summary only provides a preliminary discussion of different embodiments and corresponding points of novelty over conventional techniques. For additional details, elements, and/or possible perspectives (permutations) of the invention, the reader is directed to the Detailed Description section and corresponding figures of the present disclosure as further discussed below.

BRIEF DESCRIPTION OF FIGURES

The flow diagrams do not depict the syntax of any particular programming language. Rather, the flow diagrams illustrate the functional information one of ordinary skill in the art requires to fabricate circuits or to generate computer software to perform the processing required in accordance with the present invention. It should be noted that many routine program elements, such as initialization of loops and variables and the use of temporary variables, are not shown. It will be appreciated by those of ordinary skill in the art that unless otherwise indicated herein, the particular sequence of steps described is illustrative only and can be varied without departing from the spirit of the invention. Thus, unless otherwise stated the steps described below are unordered meaning that, when possible, the steps can be performed in any convenient or desirable order.

The foregoing will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 5 illustrates techniques to determine the corresponding first coordinate.

FIG. 7 illustrates display options for the corresponding first coordinate.

FIG. 8 illustrates improvements, which are enabled by implementing an organ-specific coordinate system.

FIG. 11 illustrates the adrenal gland and two different organ specific coordinate systems.

FIG. 13 illustrates the plotting of organ specific voxel coordinates and their associated data units.

DETAILED DESCRIPTION OF FIGURES

Some aspects, features and implementations described herein may include machines such as computers, electronic components, optical components, and processes such as computer-implemented steps. It will be apparent to those of ordinary skill in the art that the computer-implemented steps may be stored as computer-executable instructions on a non-transitory computer-readable medium. Furthermore, it will be understood by those of ordinary skill in the art that the computer-executable instructions may be executed on a variety of tangible processor devices. For ease of exposition, not every step, device or component that may be part of a computer or data storage system is described herein. Those of ordinary skill in the art will recognize such steps, devices and components in view of the teachings of the present disclosure and the knowledge generally available to those of ordinary skill in the art. The corresponding machines and processes are therefore enabled and within the scope of the disclosure.

Figure 1:
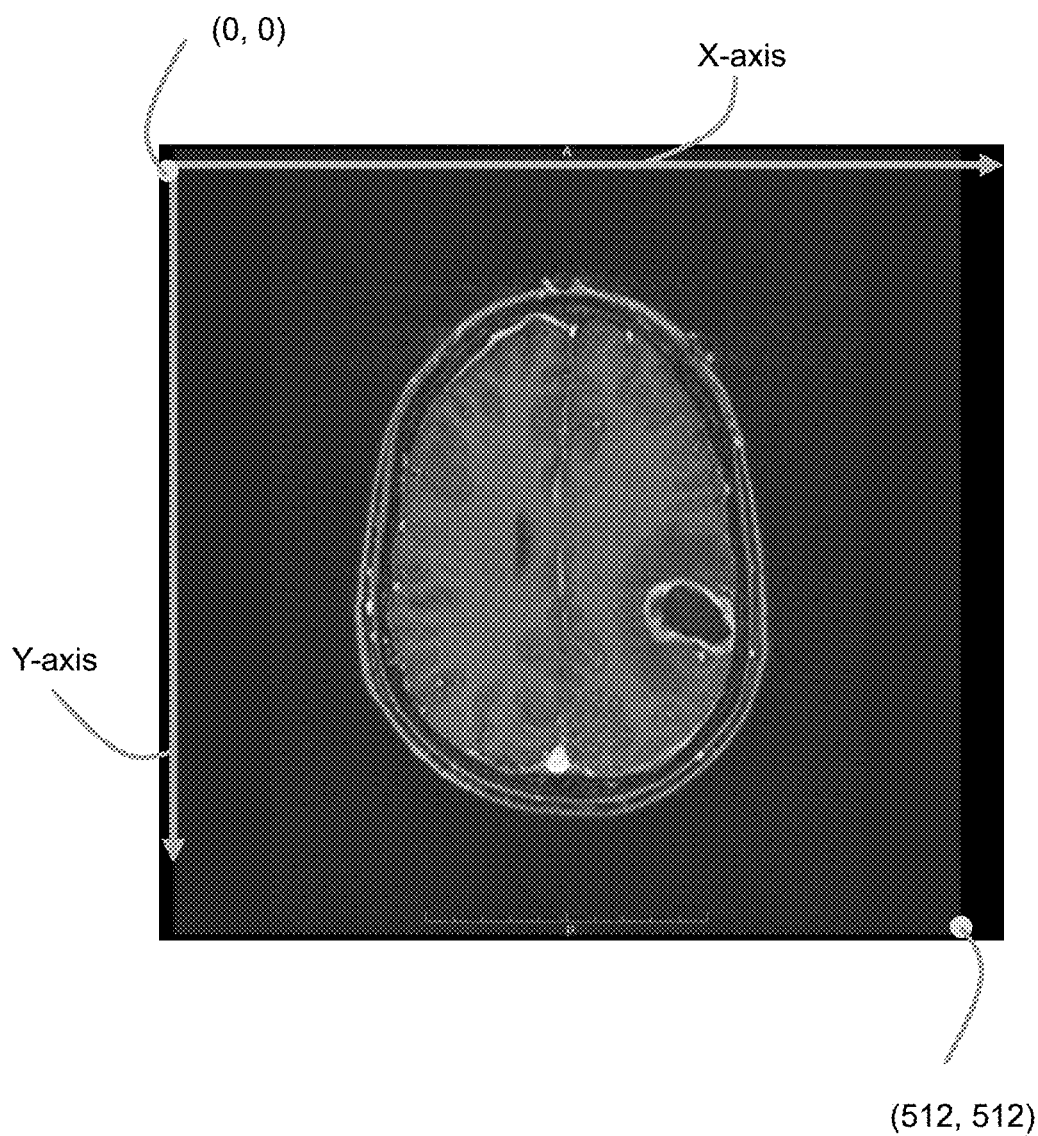
FIG. 1 illustrates prior art showing the current coordinate system for a cross-sectional imaging examination.

FIG. 1 illustrates prior art showing the current coordinate system for a cross-sectional imaging examination. Currently in 2019, typical radiology picture archiving communication systems (PACS) systems commonly display the (x,y) value and the slice number (relates to z-coordinate). There is no value whatsoever for the radiologist to look up at the screen and study the (x,y) values for a given slice. The radiologist cares about what he/she sees on the screen specifically the anatomic structures and associated intensity unit, but does not care about (x,y) coordinate. If the (x,y) coordinates were shifted a few mm away, it would have no consequence. In other words, the diagnostic radiologist studies the anatomy and grayscales and searches for pathology. When a radiologist sees a finding, he measures the grayscale (e.g., intensity units) and looks at the margins, shape, etc. But, there is no interpretation value whatsoever where the imaging finding falls within the 512×512 matrix. This image was displayed using Osirix software suite, which uses axes as displayed above.

Figure 2A:
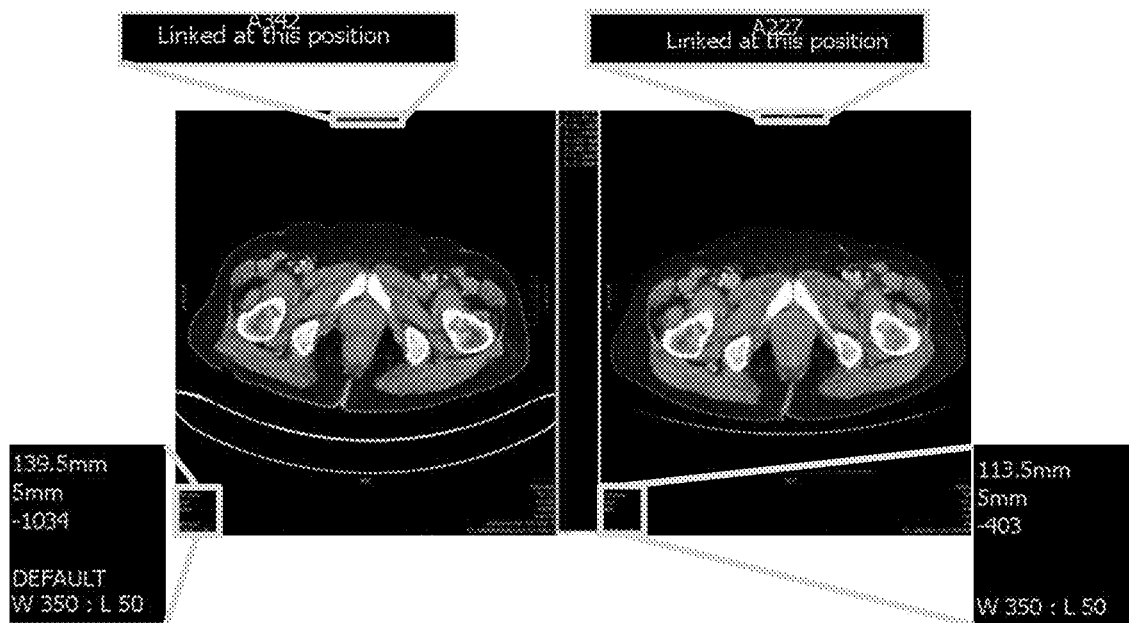
FIG. 2A illustrates the prior art system of localizing.

FIG. 2A illustrates the prior art system of localizing. Localization is used by radiologists to improve comparison between scans from two different time points. To accomplish this, the user scrolls to a slice on a first examination. Next, the radiologist scrolls to the similar slice on the second examination. In this example, a radiologist has performed the "link" command at the level of the ischial tuberosity on both the left image (from 2019) and the right image (from 2018). Next, the radiologist performs the "link" command. Next the radiologist scrolls on the first examination and the second examination moves along with it, an example of which is shown in FIG. 2B below.

Figure 2B:
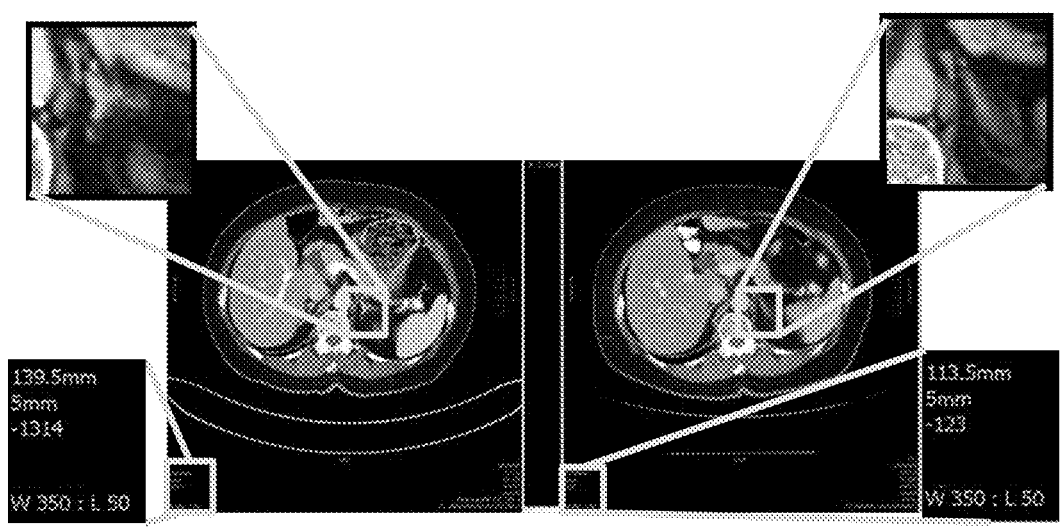
FIG. 2B illustrates scrolling with a localizing link.

FIG. 2B illustrates scrolling with a localizing link. In this example, a radiologist has scrolled superiorly from the level of the ischial tuberosity, which was performed on the 2019 imaging examination. In the 2019 exam, scrolling through 56 slices (as compared to FIG. 2A) has occurred and the position moved from position −1034 to position −1314, which is equal to 280 mm (56 slices, each slice is 5 mm thick). See text from the image above. In the 2016 exam, a distance of 280 mm (56 slices, each slice is 5 mm thick) have also been traversed. It is important to note that at this new level, the adrenal glands are not lined up. Specifically, the left adrenal gland appears lambda shaped in 2019 and linear in 2020. The radiologist has to perform manual override by unlinking and scrolling on only one of the examinations to re-align the studies.

Figure 3:
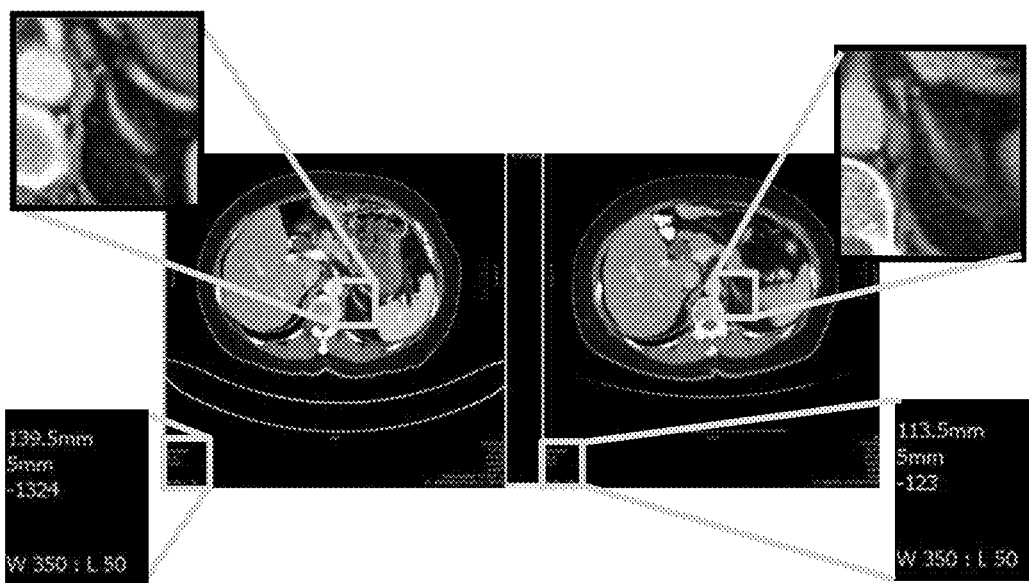
FIG. 3 illustrates a radiologist's process for re-aligning the two different CT examinations.

FIG. 3 illustrates a radiologist's process for re-aligning the two different CT examinations. A radiologist needs to "unlink" the two imaging examinations. Then, manually scroll on one of the imaging examinations. In this example, the radiologist scrolled two additional slices (58 in total) from the ischial tuberosity on the 2019 examination. After doing so, the left adrenal glands became aligned. The process of linking and unlinking can be performed to scroll through similar slices during viewing.

Figure 4:
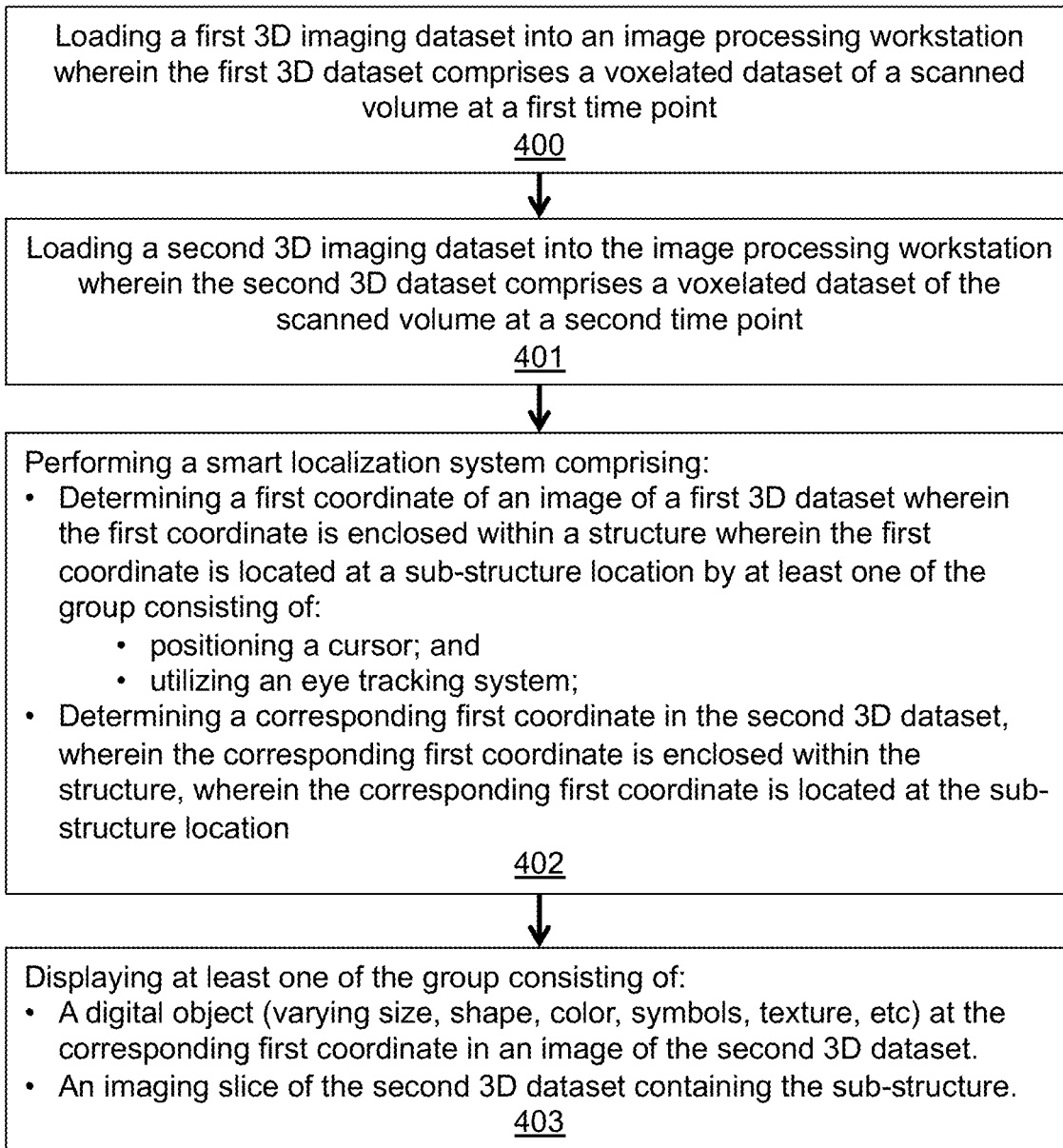
FIG. 4 illustrates the smart localization system.

FIG. 4 illustrates the smart localization system. 400 illustrates a processing block of loading a first 3D imaging dataset into an image processing workstation wherein the first 3D dataset comprises a voxelated dataset of a scanned volume at a first time point. An option is to perform segmentation of the first 3D imaging dataset at the first time point. This is useful by helping the smart localization system understand where exactly the user is looking (e.g., which structure). 401 illustrates a processing block of loading a second 3D imaging dataset into the image processing workstation wherein the second 3D dataset comprises a voxelated dataset of the scanned volume at a second time point. The second 3D imaging dataset can also be segmented, for reasons discussed below. 402 illustrates a processing block of performing a smart localization system comprising: determining a first coordinate of an image of a first 3D dataset wherein the first coordinate is enclosed within a structure wherein the first coordinate is located at a sub-structure location by at least one of the group consisting of: positioning a cursor; and utilizing an eye tracking system; and determining a corresponding first coordinate in the second 3D dataset, wherein the corresponding first coordinate is enclosed within the structure, wherein the corresponding first coordinate is located at the sub-structure location. A matching system is useful herein. For example, if a segmentation algorithm is applied to the first image and a cursor is determined to be positioned over the left adrenal gland, then the system can perform localization to the left adrenal gland. 403 illustrates a processing block of displaying at least one of the group consisting of: a digital object (varying size, shape, color, symbols, texture, etc.) at the corresponding first coordinate in an image of the second 3D dataset; and, an imaging slice of the second 3D dataset containing the sub-structure.

FIG. 5 illustrates techniques to determine the corresponding first coordinate. A first technique is by performing segmentation to determine a structure at the site of a cursor. If the localizer is inside the boundary of the left adrenal gland, then the smart localizer system would show a point inside the left adrenal gland in another image. A second technique is to use of landmarks, registration points, pseudoregistration points. Examples of landmarks would include a single coarse calcification within the spleen, which could readily be recognized. An example of registration point would include the center point of an organ. An example of a pseudoregistration point would be a point that has a defined distance between two registration points. A third technique is to use of an organ-specific coordinate system. An organ-based coordinate system can be established to improve localization by defining precise coordinates within an organ. For example, a spherical coordinate system can be performed for the liver wherein the origin is defined as the center point. A fourth technique is to perform an artificial intelligence algorithm, which utilizes training data comprises sets of longitudinal 3D imaging examinations with embedded localization points (e.g., an example would be a CT dataset from 2019 with a point on a left adrenal gland and a CT dataset from 2018 with a corresponding point on the left adrenal gland). A key point of novelty is the use of point and corresponding point as part of the training dataset. Techniques include those discussed in U.S. patent application Ser. No. 16/939,192, Radiologist Assisted Machine Learning, which is incorporated by reference in its entirety.

Figure 6A:
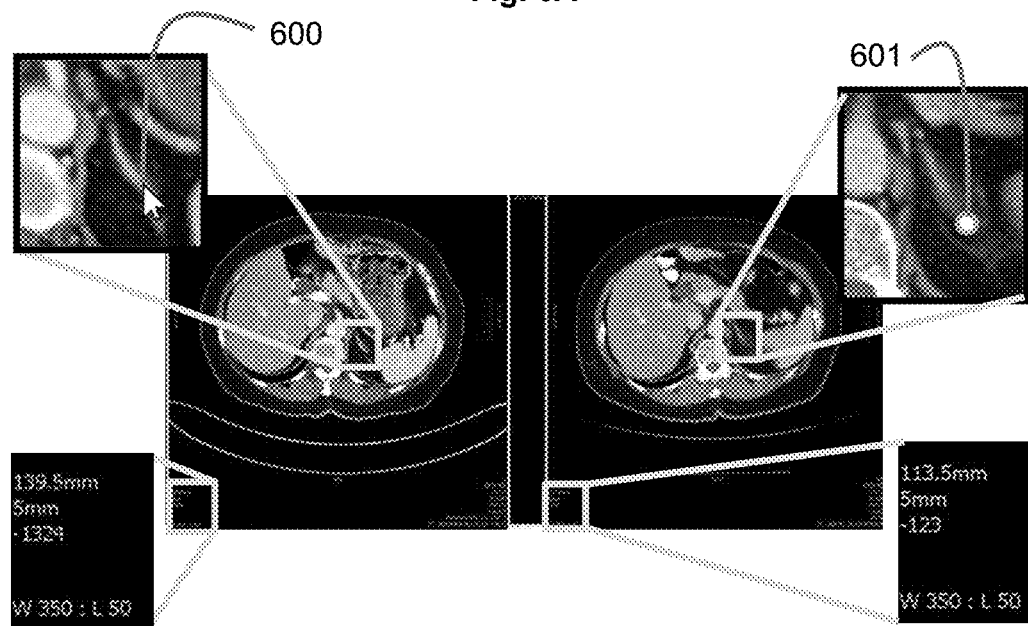
FIG. 6A illustrates a first example of the smart localization system wherein the first coordinate is determined by a cursor.

FIG. 6A illustrates a first example of the smart localization system. A PACS display is shown with a first CT scan of the abdomen from 2019 on the left and a second CT scan of the abdomen from 2018 on the right. 600 illustrates a cursor positioned on the 2019 image at a first sub-structure location (posterolateral limb) on the structure (adrenal gland). 600 illustrates a digital object positioned on the 2018 image at the corresponding first sub-structure location (posterolateral limb) on the structure (adrenal gland).

Figure 6B:
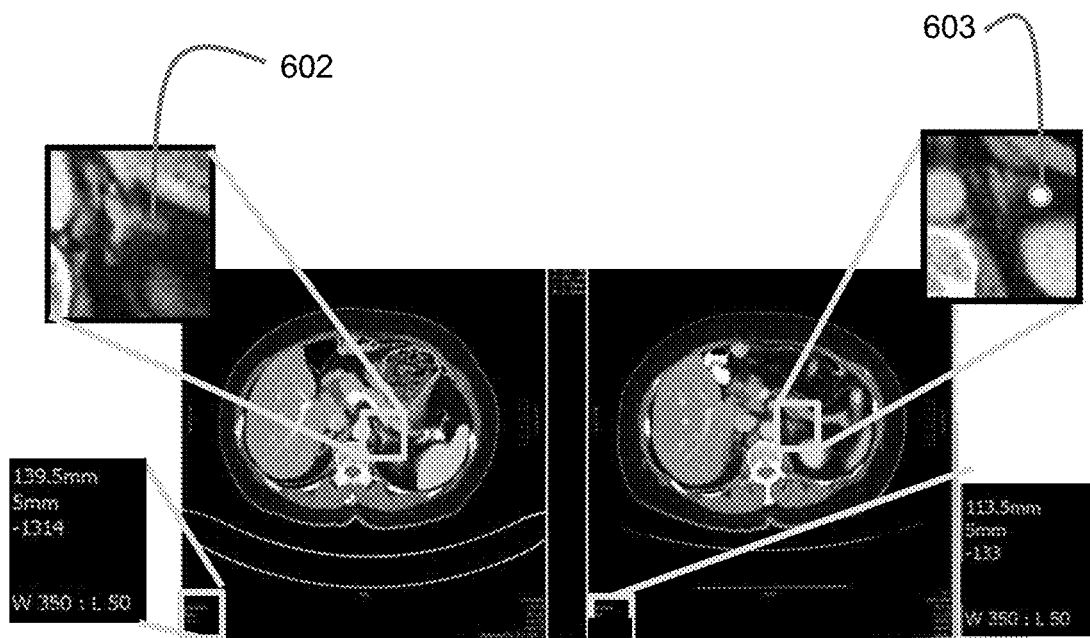
FIG. 6B illustrates a first example of the smart localization system wherein the first coordinate is determined by a fixation location.

FIG. 6B illustrates a first example of the smart localization system wherein the first coordinate is determined by a fixation location. A PACS display is shown with a first CT scan of the abdomen from 2019 on the left and a second CT scan of the abdomen from 2018 on the right. 602 illustrates the site of a fixation location positioned on the 2019 image at a first sub-structure location (posterolateral limb) on the structure (adrenal gland). 603 illustrates a digital object positioned on the 2018 image at the corresponding first sub-structure location (posterolateral limb) on the structure (adrenal gland). As soon as the user looks over to the second image, the eye tracking system displays the digital object on the second screen at a location corresponding to the last fixation location on the first screen. Thus, both cursors and eye tracking systems can determine the location of the first coordinate. The eye tracking system is discussed further in U.S. patent application Ser. No. 16/842,631, A SMART SCROLLING SYSTEM, which is incorporated by reference in its entirety.

FIG. 7 illustrates display options for the corresponding first coordinate. A table is shown with display options for the digital object for the corresponding first coordinate. Regarding the appearance of the digital object at the corresponding first coordinate, the appearance includes: variable color/grayscale (e.g., red, blue, white, yellow); variable size (e.g., 0.5 mm, 1 cm); variable shape (e.g., round, star); and, other variations (e.g., blinking, solid, etc.). Regarding the timing of display of the digital object at the corresponding first coordinate, the appearance includes: displaying the digital object at all times; and, displaying the digital object only when user is looking at the monitor displaying the first coordinate (which is advantageous because the user would not see a mobile object in the periphery of the visual field).

FIG. 8 illustrates improvements, which are enabled by implementing an organ-specific coordinate system. First, accurate voxel-by-voxel analysis is enabled. The current system mitigates errors in registration because a voxel at a first coordinate on a first exam can be compared with a voxel at a corresponding first coordinate on a second exam. This enables a comparative analysis of interval change between voxel and/or cluster of voxels at the first imaging examination with voxel and/or cluster of voxels at the second examination (e.g., generating organ-specific coordinate system so that each voxel in the segmented organ has a specific coordinate that is reproducible within the organ). Second, includes an enhanced accuracy during radiation treatment. An organ-specific coordinate system can be established. It is anticipated that various researchers and professional societies will establish preferred coordinate systems for each organ. For example, the American College of Radiology can establish a preferred coordinate system for the liver. Consider a first example. The liver could be segmented into the traditional 8 segments. The caudate lobe of the liver can have its own coordinate system with the origin at the center of the caudate lobe and a spherical coordinate system can be used. Alternatively, the entire liver could have its own coordinate system (e.g., spherical). Such organ-specific coordinate systems would enable more precise localization of small lesions (e.g., 1 cm) within the liver. Third, includes enhanced accuracy during surgery. A range of technologies are emerging in the field of surgery. For example, augmented reality systems are working their way into the operating room. In some embodiments, the augmented reality headset can be geo-registered with the organ-specific coordinate system, which will enable precision localization of a small lesion (e.g., 1 cm) within the liver.

Figure 9A:
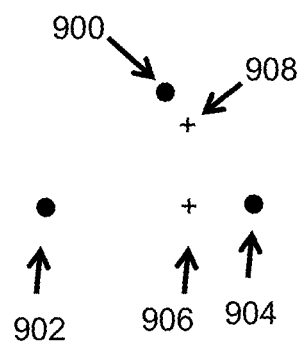
FIG. 9A illustrates identification of internal reference points at an initial examination and two spots where the user wants to localize to on a subsequent examination.

FIG. 9A illustrates identification of internal reference points at an initial examination and two spots where the user wants to localize to on a subsequent examination. 900 illustrates a first reference point. 902 illustrates a second reference point. 904 illustrates a third reference point. 906 illustrates a first area where localization to a subsequent examination is desired to occur. Note that the first localization spot 906 is in between the second reference point 902 and the third reference point 904. 908 illustrates a second area where localization to a subsequent examination is desired to occur.

Figure 9B:
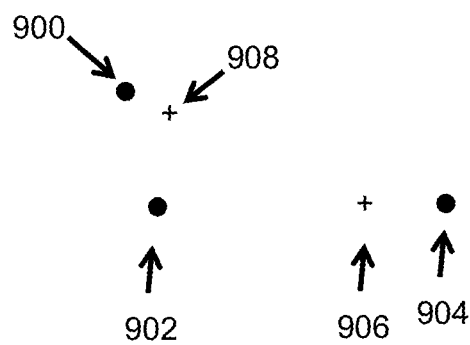
FIG. 9B illustrates identification of internal reference points at a subsequent examination with two spots where the user has localized to as compared to the initial examination.

FIG. 9B illustrates identification of internal reference points at a subsequent examination with two spots where the user has localized to as compared to the initial examination. 900 illustrates a first reference point. 902 illustrates a second reference point. 904 illustrates a third reference point. 906 illustrates a first localization spot to the prior examination (906 as shown in FIG. 9A). Note that the first localization spot 906 on FIG. 9B subsequent examination is in between the second reference point 902 and the third reference point 904 and also note that this is in a very similar position as compared to FIG. 9A, right in between the second reference point 902 and the third reference point 904. The preferred embodiment would be to place the perform a linear transform to determine the location of the first localization spot 906. To teach this, assume at the first time point in FIG. 9A that the distance between the second reference point 902 and the third reference point 904 is 4 cm and the first localization spot 906 is clicked at a location exactly 3 cm from the second localization spot 902 and 1 cm from the third localization spot 904 and along the line connecting the second localization spot 902 and the third localization spot 904. Also, assume at the second time point in FIG. 2B that the distance between the second reference point 902 and the third reference point 904 is now 6 cm. If the first localization spot 906 should appear at a location exactly 4.5 cm from the second localization spot 902 and 1.5 cm from the third localization spot 904 and along the line connecting the second localization spot 902 and the third localization spot 904. Also, note that a second localization spot 908 is immediately above the first localization spot 906 and note the position of the first reference point 900 in FIG. 9A. Note that the first reference point 900 has shifted to the left and so too has the second localization spot 908, also moving to the left. A linear transformation could be performed. Alternatively, a non-linear transformation could also be performed. In essence, this method provides registration points and performs transformations for precision localization between multiple cross-sectional imaging examinations. Ultimately, this system can also perform precision markup of lesions, enabling precision tracking of lesions and improved communication between radiologists. In some embodiments, the registration spots represent distinguishable features (e.g., coarse calcifications) in images. Also, it should be noted that the registration spots can be used in conjunction with the coordinate systems, as discussed elsewhere in this patent.

Figure 10A:
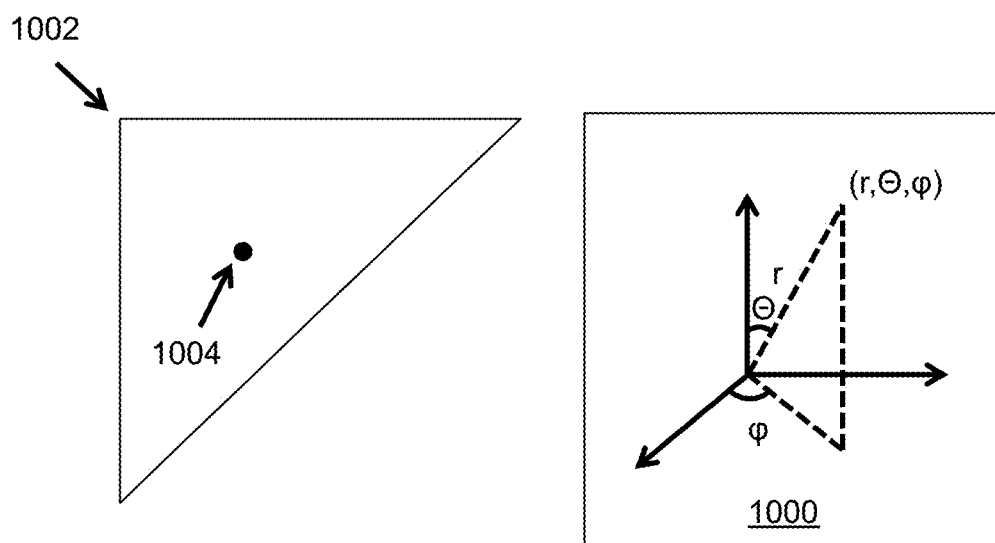
FIG. 10A illustrates the liver and an example anatomic structure specific coordinate system.

FIG. 10A illustrates the liver and an anatomic structure specific coordinate system (could also be called "organ specific coordinate system"). An example anatomic structure specific coordinate system 1000 is illustrated. The liver 1002 is illustrated. The center coordinate 1004 of the liver is illustrated at (0,0,0). All voxels within the imaging volume are assigned a coordinate within the anatomic structure specific coordinate system. This is important because a radiologist or surgeon could give a precise location. Current example descriptors for localizing a tumor include: "tumor is located at the upper pole of the kidney"; "tumor is located in the right lower thyroid lobe"; "tumor is located in the dome of the liver". This patent provides a precision method to describe location. For example, assume that the center of the liver is located at (0,0,0) and the language would in the preferred embodiment of this patent states "liver tumor coordinate of (4.4 cm, 90 degrees, 70 degrees)." This precision description is supplemented by the fact that subsequent examinations could physically load an annotation at this coordinate to provide a more comprehensive examination. This is specifically important because sometimes a tumor disappears after a first set of chemotherapy is delivered. And, it isn't until many examinations later when it comes back. There could have been 20 or more sites of tumor on an exam from years ago, but on the recent examinations only 5 sites of tumor. So, the radiologist focuses on looking at the 5 sites of tumor and could potentially miss the fact that some of the other sites present on the remote scan from years ago are coming back. This organ-specific coordinate system is much more useful and effective than an (x,y,z) coordinate system illustrated in FIG. 1 that the radiologist doesn't even look at nor care about. This coordinate system is so useful in fact because even if an organ (e.g., liver) moves on a subsequent examination, the organ specific coordinate will remain the same and the voxels within the organ specific coordinate system will remain the same.

Figure 10B:
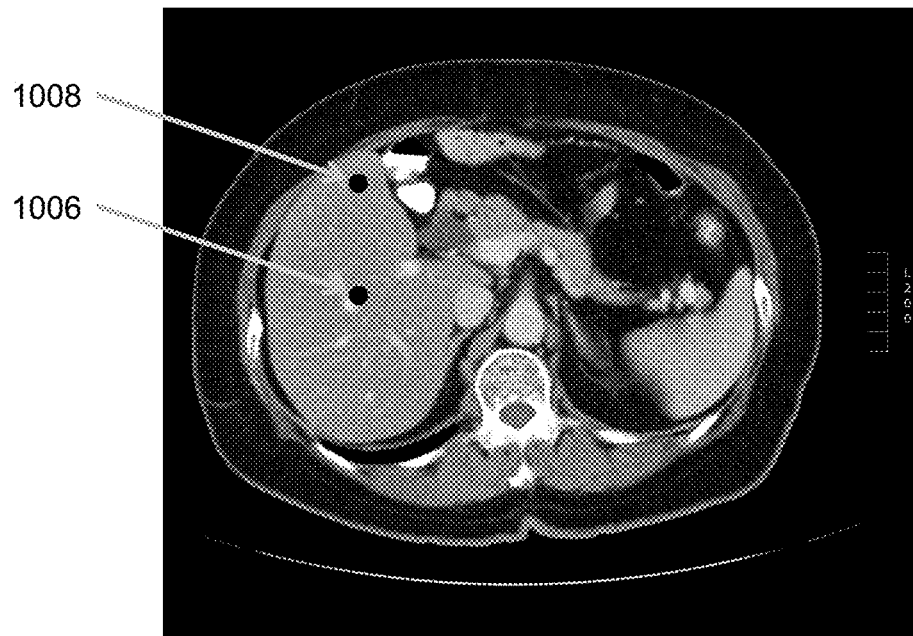
FIG. 10B illustrates a CT image of the liver and example coordinate of a voxel in the liver.

FIG. 10B illustrates a CT image of the liver and example coordinate of a voxel in the liver. 1006 illustrates the origin of the liver. 1008 illustrates an arbitrary point within the liver, whose coordinates are (r=7.4 cm, y=90 degrees, 0=0 degrees).

FIG. 11 illustrates the adrenal gland and two different organ specific coordinate systems. It should be noted that a range of coordinate systems can be used for the various organs in the body. An example organ specific coordinate system 1100, which is a spherical coordinate system is illustrated. The adrenal gland 1102 is illustrated. The center coordinate 1104 of the adrenal gland is illustrated, both within the adrenal gland 1102 and within the organ specific coordinate system 1100. In the preferred embodiment, the coordinate at the center of each organ specific coordinate system would be (0,0,0). Note that a unique coordinate system would be performed for each organ (e.g., liver has its liver specific coordinate system with center at (0,0,0), pancreas has its pancreas specific coordinate system with center at (0,0,0), etc.). This is the most straight forward strategy for an organ specific coordinate system would be to implement a conventional coordinate system, such as Cartesian coordinate system; Cylindrical coordinate system; Polar coordinate system; and, Spherical Coordinate system. One of the limitations of a spherical coordinate system, however, is the fact that for an organ like the adrenal gland which has "limbs" or "arms", is the fact that portions of it could be bent or shifted in position between scans. To overcome this, more complex mathematical models can and should be implemented. Specifically, the adrenal gland "fingers" commonly curve over distance from the center and the amount of curvature is variable from scan to scan. This can be related to the amount of mass effect on the adrenal gland from other adjacent organs, or possibly patient positioning. An example mathematical model of the adrenal gland can be performed by plotting a centerline 1106 along each limb. The superior limb 1108 of the adrenal gland is illustrated. Then each voxel could be plotted as distance along the center line 1106 plus orthogonal distance and direction away from the center line 1106. For example, voxel 1110 and orthogonal distance 1112 is shown. 1114 is an example of a course calcification, which can be used as a reference point. This coordinate system could also be applied to tumors for precision analysis. For distinctly bilobed structures (e.g., a tumor shaped as two balls connected by a thin band, a dual coordinate system could be established. The purpose of this note that each segmented structure should have its own unique organ specific coordinate that can be tracked over time to determine interval change. Since some tissues are quite deformable, internal ratios need to be established with this model (e.g., such as the making nipple a 0 and the chest wall a 1 and if the lesion is located at 90% the way back it is given a 0.9 ratio). So, a coordinate system for this would be $(r,\Theta,\varphi)$. Such a system would internally correct for amount of deformation (flattening vs. elongating) of the breast tissue. This overall process serves to provide pinpoint precision coordinates for a specific spot in an anatomic feature. Ultimately, the entire body will be mapped with pinpoint voxel-by-voxel accuracy.

Figure 12:
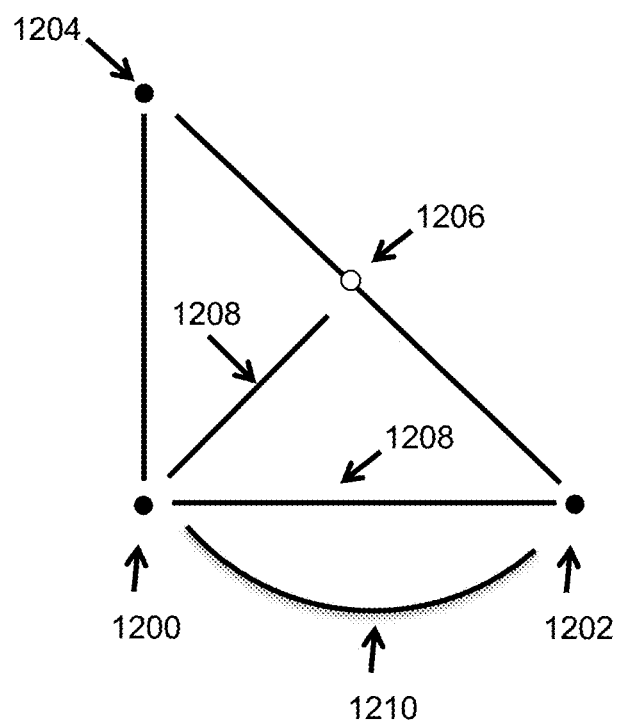
FIG. 12 illustrates reference points, pseudoreference points and ensuing analysis.

FIG. 12 illustrates reference points, pseudoreference points and ensuing analysis. 1200 illustrates a first reference point. 1202 illustrates a second reference point. 1204 illustrates a third reference point. 1206 illustrates a pseudoreference point. Reference points, as defined in this patent specification, are anatomic features that can be mapped over multiple examinations. A pseudoreference point is defined as a location which does not have any specific anatomic feature that is easily recognizable but can be used to assist with analysis. For example, measurements and voxel analysis can be performed along the distances from any pair of reference points, such as in between the first reference point 1200 and the second reference point 1202. The analysis can be in a linear fashion, such as shown in 1208. Alternatively, the analysis can be performed in a curvilinear fashion, such as is shown in 1210. Note that curvilinear fashion analysis would need to have an orientation and direction. The analysis that needs to be performed is the length, single or multiple voxel analysis, such as examining data units (e.g., Hounsfield Units) and other trajectories. Additionally, analysis can be performed between two pseudoreference points, a pseudoreference point and a reference point, such as is shown by 1208 in between the first reference point 1200 and the pseudoreference point 1206. This patent provides a method therefore of also using artificially created pseudoreference points when there are no reliable, reproducible anatomic features readily available for analysis. This process can be used with U.S. patent application Ser. No. 16/195,251 Interactive voxel manipulation strategies in volumetric medical imaging enables virtual motion, deformable tissue, and virtual radiological dissection connective tissue properties, which is incorporated by reference in its entirety. For example, certain connective tissues can be modeled in association with both reference points and pseudoreference points. Another embodiment will be to perform precision surgical guidance and radiology oncology treatment.

FIG. 13 illustrates the plotting of organ specific voxel coordinates and their associated data units. Note that an anomaly is seen on time point #3 for the organ specific voxel coordinate located at (0.1 mm, 0,0). This is an illustrative chart showing that voxels can be analyzed by their organ specific coordinate system.

Figure 14A:
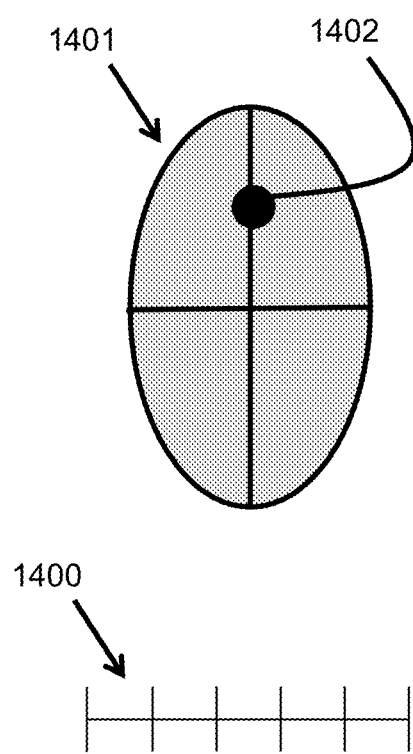
FIG. 14A illustrates a specific lesion in an organ.

FIG. 14A illustrates a specific lesion in an organ. 1400 illustrates a 5 cm distance scale. 1401 illustrates a kidney of a patient at 5 years old. Note that the kidney 1401 is approximately 5 cm in maximum dimension. 1402 illustrates a lesion within the kidney. A coordinate system can be established, such as ("percentage from origin to periphery of organ", $\varphi$, $\Theta$). For instance, lesion 1402 would be located at coordinate (50%, 0 degrees, 90 degrees). Additionally, data on the distance could also be included (50%, 2.5 cm, 0 degrees, 90 degrees).

Figure 14B:
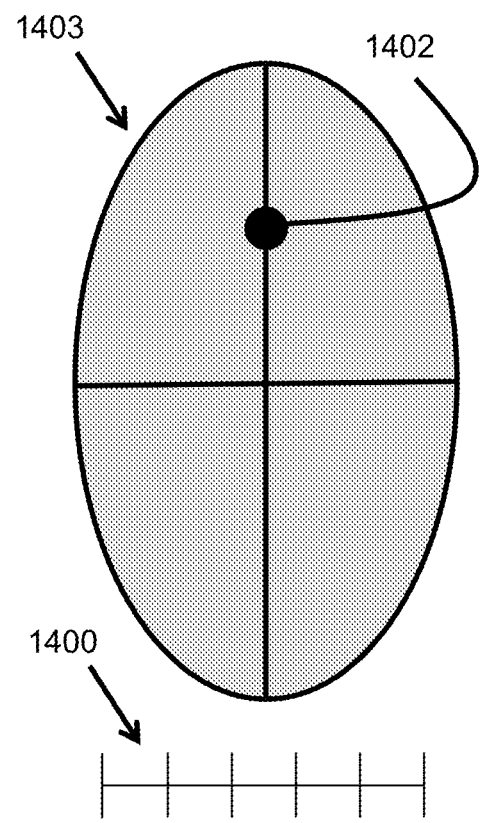
FIG. 14B illustrates how a coordinate system can track a lesion in a growing organ.

FIG. 14B illustrates how a coordinate system can track a lesion in a growing organ. Note that the kidney 1403 is approximately 10 cm in maximum dimension, in this patient who is now 15 years old. The question is asked "did the lesion at 1402 change in size?" To answer this, it is first necessary to track the location of the lesion. Ideally, a coordinate system would be able to find it even though the patient has grown from age 5 to age 15. The coordinate system established in FIG. 14A illustrates that lesion 1402 is still at coordinate (50%, 0 degrees, 90 degrees).

Figure 15A:
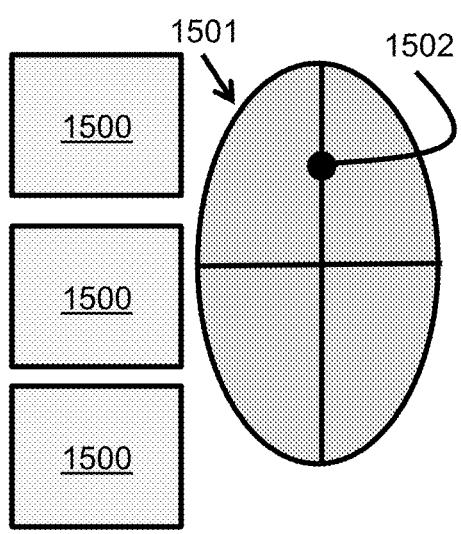
FIG. 15A illustrates a specific lesion in an organ, wherein the organ is in a first orientation.

FIG. 15A illustrates a specific lesion in an organ, wherein the organ is in a first orientation. 1500 illustrates vertebral bodies, which are used as an external reference point for orientation purposes. 1501 illustrates a kidney of a patient in 2018. 1502 illustrates a lesion within the kidney. A coordinate system can be established, such as ("percentage from origin to periphery of organ", $\varphi$, $\theta$). For instance, lesion 1502 would be located at coordinate (50%, 0 degrees, 90 degrees).

Figure 15B:
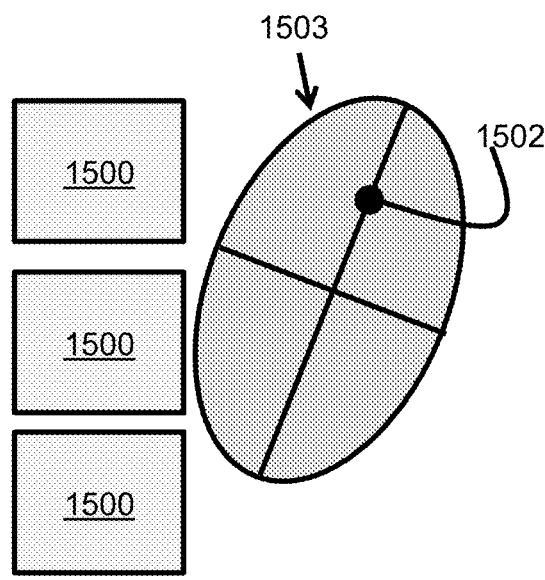
FIG. 15B illustrates how an organ specific coordinate system can track a lesion in a subsequent scan wherein the organ has a different orientation.

FIG. 15B illustrates how an organ specific coordinate system can track a lesion in a subsequent scan wherein the organ has a different orientation. 1500 illustrates vertebral bodies, which are used as an external reference point for orientation purposes. 1503 illustrates the kidney in a new orientation as compared to the vertebral bodies in a 2019 scan. In using the organ-specific coordinate system, the lesion 1502 would be still located at coordinate (50%, 0 degrees, 90 degrees), which provides improved tracking as compared to the coordinate system used in FIG. 1.

Figure 16A:
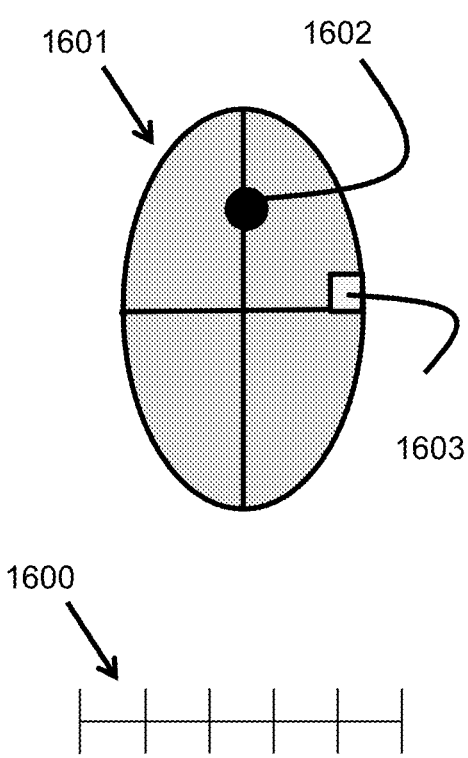
FIG. 16A illustrates a specific lesion in an organ, wherein the organ is in a first configuration.

FIG. 16A illustrates a specific lesion in an organ, wherein the organ is in a first configuration. 1600 illustrates a 5 cm distance scale. 1601 illustrates a kidney of a patient in 2018, wherein the kidney 1601 has a first morphologic configuration. 1602 illustrates a lesion within the kidney. A coordinate system can be established, such as ("percentage from origin to periphery of organ", $\varphi$, $\Theta$). For instance, lesion 1602 would be located at coordinate (50%, 0 degrees, 90 degrees). Voxelation of the kidney can be performed so that voxels contain similar tissue over multiple examinations. For example, a chunk (or portion or section) of tissue can be assigned to voxel 1603, which is isotropic.

Figure 16B:
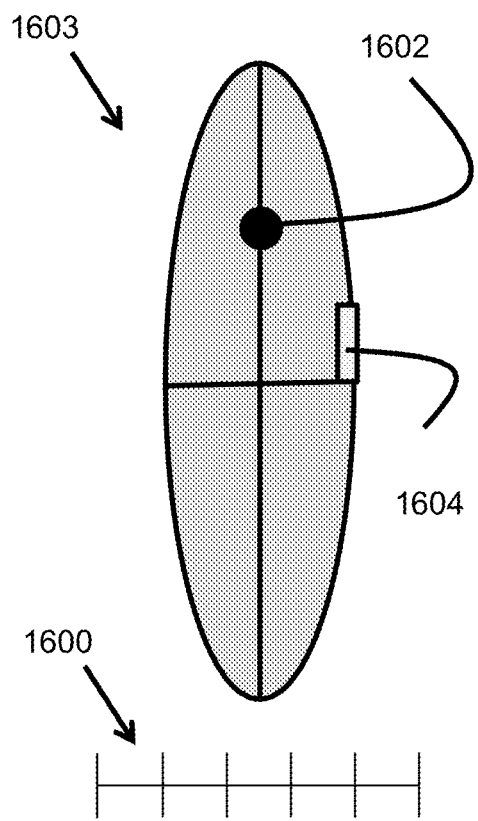
FIG. 16B illustrates how an organ specific coordinate system can track a lesion in a subsequent scan wherein the organ has a different configuration.

FIG. 16B illustrates how an organ specific coordinate system can track a lesion in a subsequent scan wherein the organ has a different configuration. 1600 illustrates a 5 cm distance scale. 1603 illustrates the kidney in a new configuration as compared to the vertebral bodies in a 2019 scan. The new configuration could be due to conditions such as external mass effect on the kidney 1603. In using the organ-specific coordinate system, the lesion 1602 would be still located at coordinate (50%, 0 degrees, 90 degrees), which provides improved tracking as compared to the coordinate system used in FIG. 1. Voxelation of the kidney can be performed so that voxels contain similar tissue over multiple examinations. For example, the same chunk (or portion or section) of tissue assigned to isotropic voxel 1603 can be assigned to voxel 1604, which is anisotropic. This allows comparison of similar sections of tissue while the morphology of the organ changes. Such a process improves conventional voxel-based morphometry (e.g., in neuroimaging) because it accounts for changes in configuration of organs in between examinations.

Figure 17:
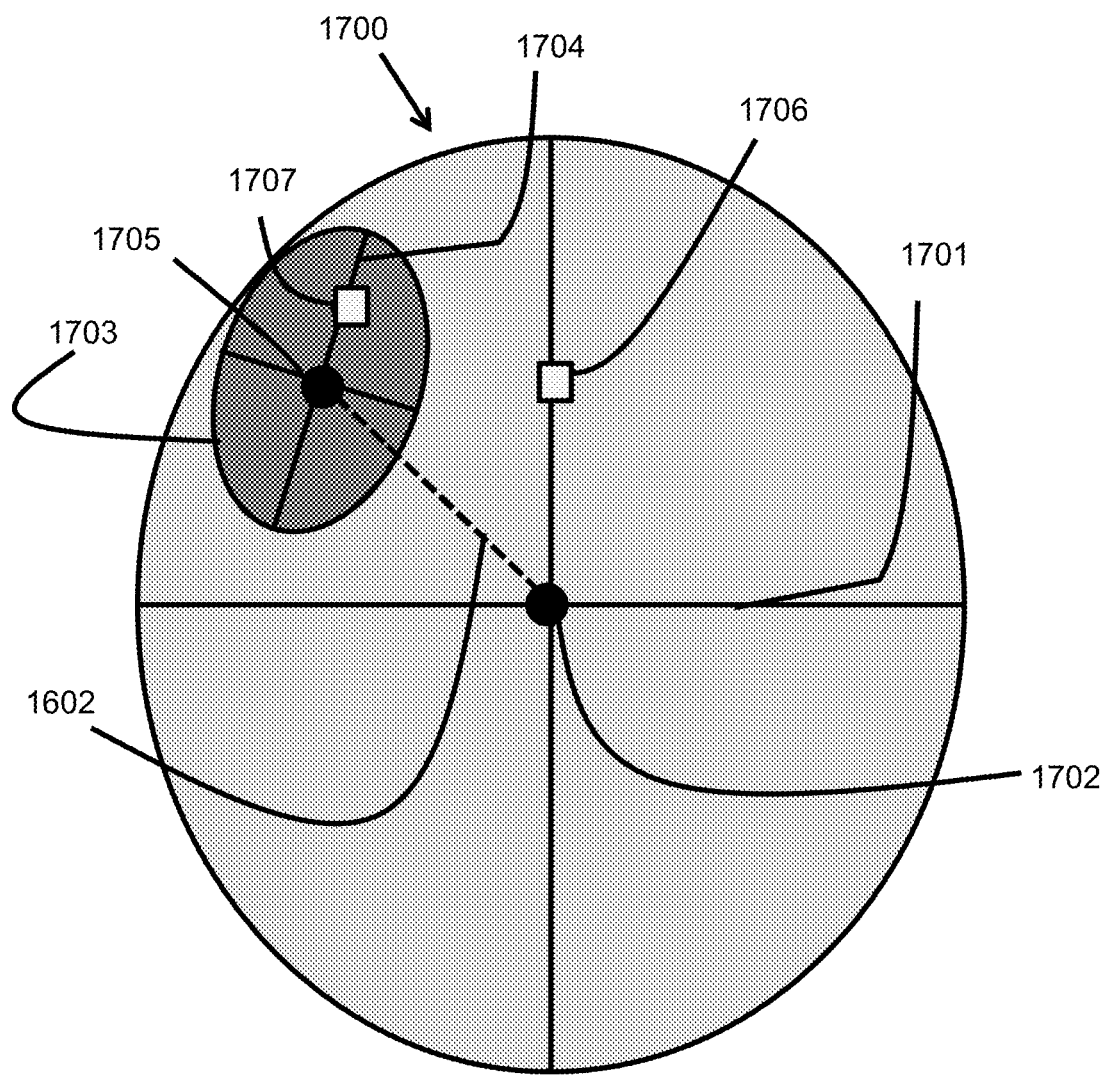
FIG. 17 illustrates multiple coordinate systems in a single structure.

FIG. 17 illustrates multiple coordinate systems in a single structure. 1700 illustrates a structure (e.g., tumor). 1701 illustrates an anatomic structure specific coordinate system (e.g., coordinate system described in FIG. 14A and FIG. 14B). 1702 illustrates an origin of the coordinate system 1701. 1703 illustrates a sub-structure within the tumor, such as a solid nodular component. 1704 illustrates a coordinate system of the sub-structure. 1705 illustrates an origin of the coordinate system of the sub-structure 1704. 1706 illustrates a voxel pertaining to the structure 1700. 1707 illustrates a voxel pertaining to the sub-structure 1703. 1708 illustrates a distance from the origin of the structure 1702 to the origin of the sub-structure 1705. To describe a coordinate system within the nodule, a first coordinate system of the structure can reference a second coordinate system of the sub-structure.

Figure 18:
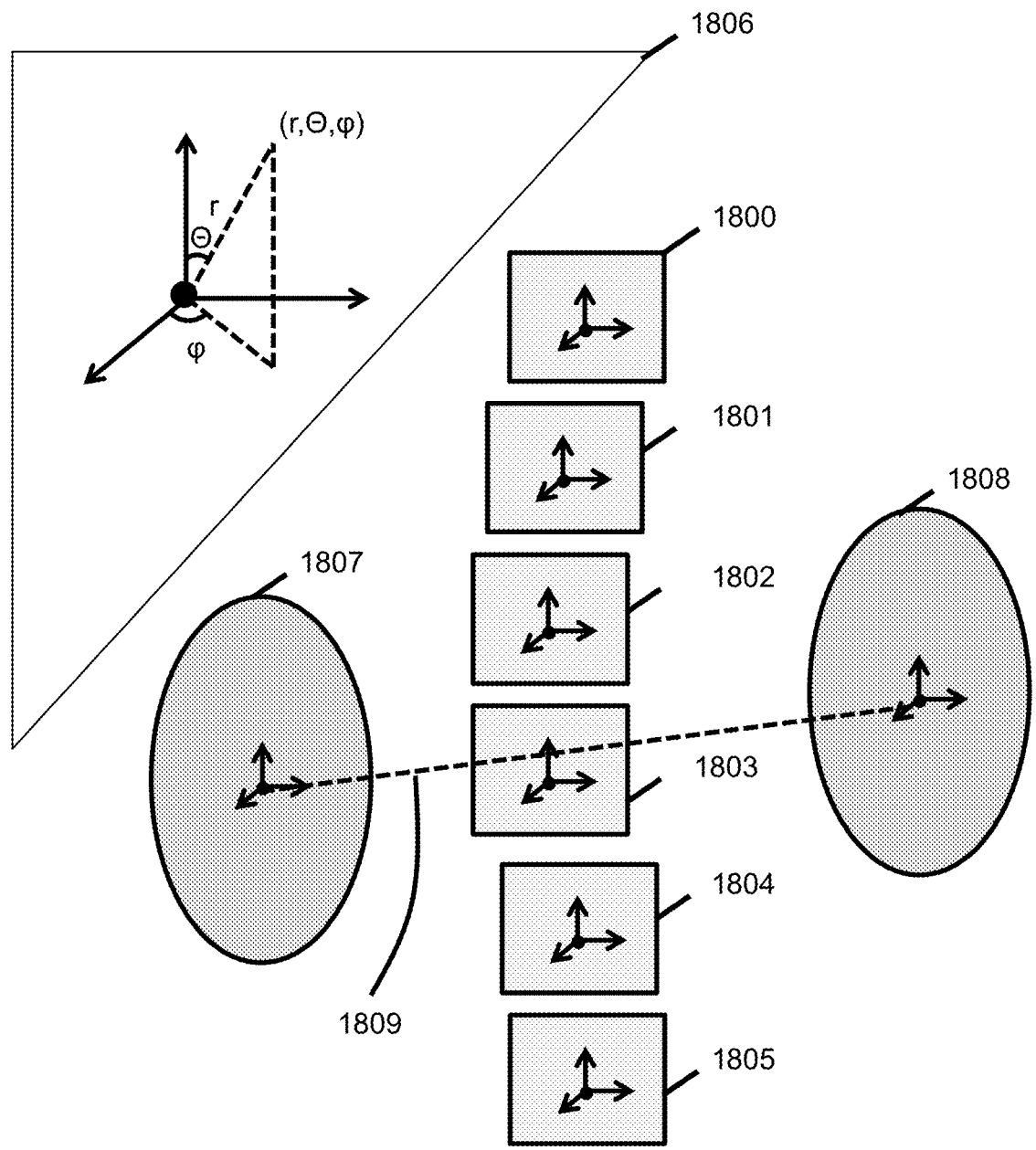
FIG. 18 illustrates the use of an anatomic structure-specific coordinate system for each segmented structure in an imaging examination.

FIG. 18 illustrates the use of an anatomic structure-specific coordinate system for each segmented structure in an imaging examination. 1800 illustrates a first vertebral body, which has an organ-specific coordinate system. 1801 illustrates a second vertebral body, which has an organ-specific coordinate system. 1802 illustrates a third vertebral body, which has an organ-specific coordinate system. 1803 illustrates a fourth vertebral body, which has an organ-specific coordinate system. 1804 illustrates a fifth vertebral body, which has an organ-specific coordinate system. 1805 illustrates a sixth vertebral body, which has an organ-specific coordinate system. 1806 illustrates a liver, which has an organ-specific coordinate system. 1807 illustrates a right kidney, which has an organ-specific coordinate system. 1808 illustrates a left kidney, which has an organ-specific coordinate system. In some embodiments, precision inter-organ relationships can be performed. For example, the major axis of the kidney (as defined as the axis from the superior pole to the inferior pole can be performed for each kidney. A longitudinal analysis of the relationship between the right kidney and the left kidney can be performed over multiple examinations. For example, on a first time point, the major axis of the right kidney could be directed superior-inferior and the major axis of the left kidney could be directed in a parallel fashion (as compared to the major axis of the right kidney). On a second time point, the major axis of the right kidney could be directed superior-inferior and the major axis of the left kidney could be directed in an oblique fashion (as compared to the major axis of the right kidney). A new change in orientation could indicated pathology, such as mass effect from a growing tumor. The assigning of a structure-specific coordinate system could also be useful in a range of applications. For example, it would be able to answer a variety of questions, such as are the kidneys being pushed apart over time (e.g., by a tumor). For example, a distance from the origin of the right kidney 1807 to the left kidney 1808 is illustrated as 1809. A large amount of inter-organ relationships can be assessed by measurements. It could also help determine changes in scoliosis by precisely mapping what is happening to each vertebrae and can refine treatments. It is important to note that different segmented structures can have different organ-specific coordinate systems. For example, the rigid vertebrae can have a cartesian coordinate system. The deformable kidney could have a spherical coordinate system. The adrenal gland can be modeled with a custom coordinate system, as previously discussed.

Figure 19A:
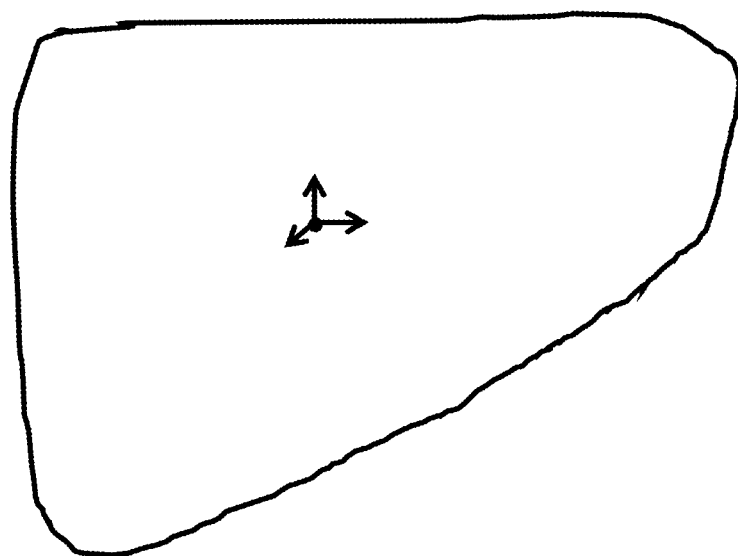
FIG. 19A illustrates a single coordinate system for the liver.

FIG. 19A illustrates a single coordinate system for the liver. The liver and a single coordinate system are shown. This would be the simplest method and is good in most situations. However, in some situations where a portion of the liver is deformed on an imaging examination (e.g., mass effect), errors could occur. In these situations, multiple coordinate systems can be used and can overcome these type errors, such as taught in FIG. 19B.

Figure 19B:
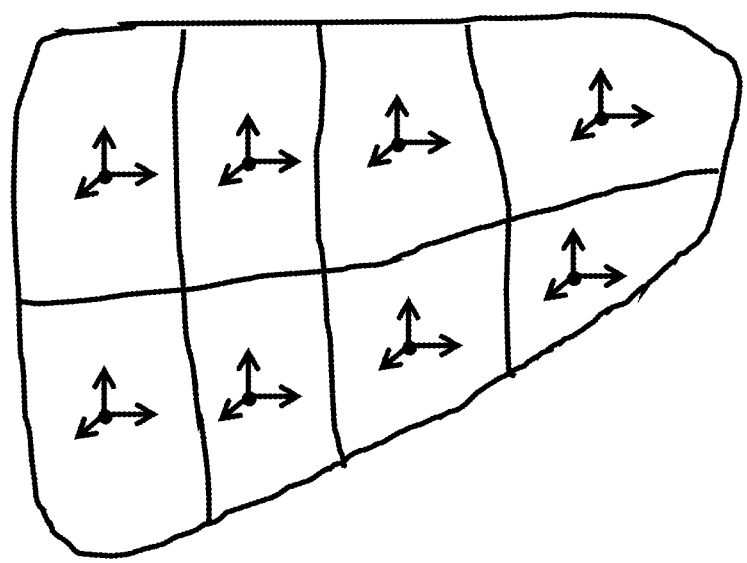
FIG. 19B illustrates a multiple coordinate systems for the liver.

FIG. 19B illustrates a multiple coordinate systems for the liver. Note that this illustration shows that the liver has been segmented into eight segments. Each segment has its own coordinate system. This is a more robust system and can provide accurate tracking of liver lesions longitudinally even in the setting of post-surgical changes or other deformities to the liver that might occur.

Throughout the entirety of the present disclosure, use of the articles "a" or "an' to modify a noun may be understood to be used for convenience and to include one, or more than one of the modified noun, unless otherwise specifically stated. Elements, components, modules, and/or parts thereof that are described and/or otherwise portrayed through the figures to communicate with, be associated with, and/or be based on, something else, may be understood to so communicate, be associated with, and or be based on in a direct and/or indirect manner, unless otherwise stipulated herein. The device(s) or computer systems that integrate with the processor(s) may include, for example, a personal computer(s), workstation(s) (e.g., Sun, HP), personal digital assistant(s) (PDA(s)), handheld device(s) such as cellular telephone(s), laptop(s), handheld computer(s), or other device(s) capable of being integrated with a processor(s) that may operate as provided herein. Accordingly, the devices provided herein are not exhaustive and are provided for illustration and not limitation. References to "a microprocessor and "a processor, or "the microprocessor and "the processor." may be understood to include one or more microprocessors that may communicate in a stand-alone and/or a distributed environment(s) and may thus be configured to communicate via wired or wireless communications with other processors, where such one or more processor may be configured to operate on one or more processor-controlled devices that may be similar or different devices. Use of such "microprocessor or "processor terminology may thus also be understood to include a central processing unit, an arithmetic logic unit, an application-specific integrated circuit (IC), and/or a task engine, with such examples provided for illustration and not limitation. Furthermore, references to memory, unless otherwise specified, may include one or more processor-readable and accessible memory elements and/or components that may be internal to the processor-controlled device, external to the processor-controlled device, and/or may be accessed via a wired or wireless network using a variety of communications protocols, and unless otherwise specified, may be arranged to include a combination of external and internal memory devices, where Such memory may be contiguous and/or partitioned based on the application.

Accordingly, references to a database may be understood to include one or more memory associations, where such references may include commercially available database products (e.g., SQL, Informix, Oracle) and also include proprietary databases, and may also include other structures for associating memory Such as links, queues, graphs, trees, with such structures provided for illustration and not limitation. References to a network, unless provided otherwise, may include one or more intranets and/or the Internet, as well as a virtual network. References hereinto microprocessor instructions or microprocessor-executable instructions, in accordance with the above, may be understood to include programmable hardware.

Unless otherwise stated, use of the word "substantially' may be construed to include a precise relationship, condition, arrangement, orientation, and/or other characteristic, and deviations thereof as understood by one of ordinary skill in the art, to the extent that such deviations do not materially affect the disclosed methods and systems. Throughout the entirety of the present disclosure, use of the articles "a" or "an' to modify a noun may be understood to be used for convenience and to include one, or more than one of the modified noun, unless otherwise specifically stated. Elements, components, modules, and/or parts thereof that are described and/or otherwise portrayed through the figures to communicate with, be associated with, and/or be based on, something else, may be understood to so communicate, be associated with, and or be based on in a direct and/or indirect manner, unless otherwise stipulated herein. Although the methods and systems have been described relative to a specific embodiment thereof, they are not so limited. Obviously, many modifications and variations may become apparent in light of the above teachings. Many additional changes in the details, materials, and arrangement of parts, herein described and illustrated, may be made by those skilled in the art. Having described preferred embodiments of the invention it will now become apparent to those of ordinary skill in the art that other embodiments incorporating these concepts may be used. Additionally, the software included as part of the invention may be embodied in a computer program product that includes a computer useable medium. For example, such a computer usable medium can include a readable memory device, such as a hard drive device, a CD-ROM, a DVD ROM, or a computer diskette, having computer readable program code segments stored thereon. The computer readable medium can also include a communications link, either optical, wired, or wireless, having program code segments carried thereon as digital or analog signals. Accordingly, it is submitted that that the invention should not be limited to the described embodiments but rather should be limited only by the spirit and scope of the appended claims.

Several features, aspects, embodiments and implementations have been described. Nevertheless, it will be understood that a wide variety of modifications and combinations may be made without departing from the scope of the inventive concepts described herein. Accordingly, those modifications and combinations are within the scope of the following claims.

The invention claimed is:

1. A method comprising:
   loading a first 3D imaging dataset into an image processing workstation wherein the first 3D dataset comprises a voxelated dataset of a scanned volume at a first time point;
   loading a second 3D imaging dataset into the image processing workstation wherein the second 3D dataset comprises a voxelated dataset of the scanned volume at a second time point;
   performing a smart localization system comprising:
      determining a first coordinate of an image of a first 3D dataset wherein the first coordinate is enclosed within a structure wherein the first coordinate is located at a sub-structure location by at least one of the group consisting of:
         positioning a cursor; and
         utilizing an eye tracking system;
      determining a corresponding first coordinate in a second 3D dataset, wherein the corresponding first coordinate is enclosed within the structure and wherein the corresponding first coordinate is located at the sub-structure location; and
   displaying at least one of the group consisting of:
      a digital object at the corresponding first coordinate in an image of the second 3D dataset; and
      an imaging slice of the second 3D dataset containing the sub-structure.

2. The method of claim 1 further comprising utilizing in the smart localization system at least one reference point within the structure comprising wherein the at least one reference point is selected from the group consisting of:
   a center point;
   a superior most point;
   an inferior most point;
   a medial most point;
   a lateral most point;
   an anterior most point;
   a posterior most point; and
   a recognizable anatomic feature.

3. The method of claim 2 further comprises wherein the at least one reference point is used for at least one of the group consisting of: volumetric analysis; and, morphologic analysis.

4. The method of claim 2 further comprising utilizing at least one pseudoreference point within the structure comprising wherein the at least one pseudoreference point is a point at a distance in between at least two reference points.

5. The method of claim 4 further comprises wherein the at least one pseudoreference point is used for at least one of the group consisting of: volumetric analysis; and, morphologic analysis.

6. The method of claim 2 further comprising utilizing in the smart localization system a coordinate system based comprising at least one of the group consisting of:
   a cartesian coordinate system;
   a cylindrical coordinate system;
   a polar coordinate system;
   a spherical coordinate system; and
   an organ specific coordinate system.

7. The method of claim 6 further comprises assigning a precision location of a lesion wherein the precision location comprises a coordinate location on the coordinate system.

8. The method of claim 6 further comprising inputting the precision location of the lesion in a radiology report.

9. The method of claim 8 further comprises generating at least two coordinate systems for the structure.

10. The method of claim 8 further comprises using the coordinate system for at least one of the group consisting of:
   a radiation treatment; and
   a surgical procedure.

11. The method of claim 6 further comprises inputting an annotation at the site of the precision location of the lesion on an image.

12. The method of claim 1 further comprising wherein when the structure changes in size from the first 3D dataset to the second 3D dataset, the determining of the corresponding first coordinate in the second 3D dataset accounts for the structure's changes in size.

13. The method of claim 1 further comprising wherein when the structure changes in configuration from the first 3D dataset to the second 3D dataset, the determining of the corresponding first coordinate in the second 3D dataset accounts for the structure's changes in configuration.

14. The method of claim 1 further comprising wherein when the structure changes in orientation from the first 3D dataset to the second 3D dataset, the determining of the corresponding first coordinate in the second 3D dataset accounts for the structure's changes in orientation.

15. The method of claim 1 further comprising:
determining a reference axis for the volume in the first 3D dataset;
determining an axis of the structure in the first 3D dataset;
determining a first angle wherein the first angle is an angle between the reference axis for the volume in the first 3D dataset and the axis of the structure in the first 3D dataset;
determining a corresponding reference axis for the volume in the second 3D dataset;
determining a corresponding axis of the structure in the second 3D dataset;
determining a second angle wherein the second angle is an angle between the corresponding reference axis for the volume in the second 3D dataset and the corresponding axis of the structure in the second 3D dataset; and
comparing the first angle with the second angle to determine an interval change.

16. The method of claim 1 further comprising performing an analysis of interval change between a voxel at the sub-structure in the first 3D dataset and a voxel at the sub-structure in the second 3D dataset.

17. The method of claim 1 further comprises determining the corresponding first coordinate by utilizing an artificial intelligence system, wherein the artificial intelligence system utilizes training data comprises sets of longitudinal 3D imaging examinations with embedded localization points.

18. A non-transitory computer readable medium having computer readable code thereon for image processing, the medium comprising:
performing a smart localization system comprising:
determining a first coordinate of an image of a first 3D dataset wherein the first coordinate is enclosed within a structure wherein the first coordinate is located at a sub-structure location by at least one of the group consisting of:
positioning a cursor; and
utilizing an eye tracking system;
determining a corresponding first coordinate in a second 3D dataset, wherein the second 3D dataset contains the structure, wherein the corresponding first coordinate is enclosed within the structure and wherein the corresponding first coordinate is located at the sub-structure location; and
displaying at least one of the group consisting of:
a digital object at the corresponding first coordinate in an image of the second 3D dataset; and
an imaging slice of the second 3D dataset containing the sub-structure.

19. An apparatus comprising:
an IO device; and
an image processor in communication with the IO device, the image processors comprising a program stored on a computer-readable non-transitory media, the program comprising instructions that:
perform a smart localization system comprising:
determining a first coordinate of an image of a first 3D dataset wherein the first coordinate is enclosed within a structure wherein the first coordinate is located at a sub-structure location by at least one of the group consisting of:
positioning a cursor; and
utilizing an eye tracking system;
determining a corresponding first coordinate in a second 3D dataset, wherein the second 3D dataset contains the structure, wherein the corresponding first coordinate is enclosed within the structure and wherein the corresponding first coordinate is located at the sub-structure location; and
display at least one of the group consisting of:
a digital object at the corresponding first coordinate in an image of the second 3D dataset; and
an imaging slice of the second 3D dataset containing the sub-structure.

* * * * *